United States Patent
McNab et al.

(10) Patent No.: US 10,004,538 B2
(45) Date of Patent: Jun. 26, 2018

(54) SURGICAL INSTRUMENT AND METHOD (71) Applicant: Warsaw Orthopedic, Inc, Warsaw, IN (US)

(72) Inventors: Jennifer G. McNab, Memphis, TN (US); Nicholas M. Benson, Cordova, TN (US); Brian A. Butler, Atoka, TN (US); Eric D. Densford, West Memphis, AR (US); Christine Joe, Evanston, IL (US); Larry T. McBride, Jr., Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 0 days. days.

(21) Appl. No.: 15/140,219

(22) Filed: Apr. 27, 2016

(65) Prior Publication Data

US 2017/0311986 A1 Nov. 2, 2017

(51) Int. Cl.
*A61B 17/70* (2006.01)
*A61B 17/68* (2006.01)

(52) U.S. Cl.
CPC ........ *A61B 17/7023* (2013.01); *A61B 17/708* (2013.01); *A61B 17/7082* (2013.01); *A61B 2017/681* (2013.01)

(58) Field of Classification Search
CPC .................................................. A61B 17/7023
See application file for complete search history.

(56) References Cited

U.S. PATENT DOCUMENTS

| | | | | |
|---|---|---|---|---|
| 1,365,532 A | * | 1/1921 | Mountain | A61F 2/64 16/340 |
| 2,077,844 A | * | 4/1937 | Leighton | B62D 17/00 188/197 |
| 3,816,854 A | * | 6/1974 | Schlein | A61F 2/3804 623/20.12 |
| 5,405,347 A | * | 4/1995 | Lee | A61B 17/6416 403/103 |
| 5,509,328 A | * | 4/1996 | Lai | B62K 21/16 280/279 |
| 5,643,263 A | * | 7/1997 | Simonson | A61B 1/00085 606/264 |
| 6,007,536 A | * | 12/1999 | Yue | A61B 17/809 606/60 |
| 6,238,396 B1 | * | 5/2001 | Lombardo | A61B 17/7052 606/251 |
| 6,296,644 B1 | * | 10/2001 | Saurat | A61B 17/7013 606/256 |
| 6,620,164 B2 | * | 9/2003 | Ueyama | A61B 17/7002 606/261 |
| 6,652,527 B2 | * | 11/2003 | Zucherman | A61K 31/37 606/249 |

(Continued)

*Primary Examiner* — Ellen C Hammond
*Assistant Examiner* — Stuart S Bray (57) ABSTRACT

A surgical instrument includes a first arm engageable with a first spinal construct disposed with a first vertebral surface. A second arm is connected with the first arm via a pivot and being engageable with a second spinal construct disposed with a second vertebral surface. The first arm is movable to rotate the first spinal construct relative to the pivot and/or the second arm is movable to rotate the second spinal construct relative to the pivot such that the first vertebral surface is moved relative to the second vertebral surface. Systems and methods of use are disclosed.

17 Claims, 11 Drawing Sheets

(56) References Cited

U.S. PATENT DOCUMENTS

| | | | | |
|---|---|---|---|---|
| 6,872,209 B2* | 3/2005 | Morrison | A61B 17/7038 | 606/278 |
| 7,517,359 B2* | 4/2009 | Drewry | A61B 17/7005 | 606/256 |
| 8,109,974 B2 | 2/2012 | Boomer et al. | | |
| 8,690,923 B2* | 4/2014 | Lynch | A61B 17/705 | 606/246 |
| 8,870,918 B2 | 10/2014 | Boomer et al. | | |
| 9,060,816 B2* | 6/2015 | Abdou | A61B 17/7068 | |
| 9,155,565 B2 | 10/2015 | Boomer et al. | | |
| 9,198,696 B1* | 12/2015 | Bannigan | A61B 17/7052 | |
| 9,204,901 B2* | 12/2015 | Black | A61B 17/7004 | |
| 2002/0138077 A1* | 9/2002 | Ferree | A61B 17/7005 | 606/258 |
| 2004/0133203 A1* | 7/2004 | Young | A61B 17/7052 | 606/253 |
| 2005/0228376 A1* | 10/2005 | Boomer | A61B 17/7013 | 606/260 |
| 2006/0009767 A1* | 1/2006 | Kiester | A61B 17/7004 | 606/258 |
| 2006/0195086 A1* | 8/2006 | Sybert | A61B 17/7005 | 606/264 |
| 2007/0118122 A1* | 5/2007 | Butler | A61B 17/7023 | 606/86 A |
| 2007/0288009 A1* | 12/2007 | Brown | A61B 17/7014 | 606/279 |
| 2008/0033434 A1 | 2/2008 | Boomer et al. | | |
| 2008/0125817 A1* | 5/2008 | Arnett | A61B 17/7002 | 606/319 |
| 2009/0281574 A1* | 11/2009 | Jackson | A61B 17/7004 | 606/264 |
| 2010/0036423 A1* | 2/2010 | Hayes | A61B 17/7025 | 606/260 |
| 2010/0217334 A1* | 8/2010 | Hawkes | A61B 17/7007 | 606/305 |
| 2010/0262187 A1* | 10/2010 | Marik | A61B 17/7004 | 606/246 |
| 2011/0098748 A1* | 4/2011 | Jangra | A61B 17/7004 | 606/278 |
| 2011/0251646 A1* | 10/2011 | Karnezis | A61B 17/7007 | 606/278 |
| 2012/0203279 A1* | 8/2012 | Walters | A61B 17/7077 | 606/252 |
| 2013/0018419 A1* | 1/2013 | Rezach | A61B 17/7076 | 606/264 |
| 2013/0103096 A1* | 4/2013 | Miller | A61B 17/7032 | 606/305 |
| 2013/0261667 A1* | 10/2013 | Cheng | A61B 17/7023 | 606/257 |
| 2014/0358181 A1* | 12/2014 | Abdou | A61B 17/7068 | 606/248 |
| 2016/0367292 A1* | 12/2016 | Nichols | A61B 17/7041 | |
| 2016/0374728 A1* | 12/2016 | Kim | A61B 17/7011 | 606/256 |

* cited by examiner

SURGICAL INSTRUMENT AND METHOD

TECHNICAL FIELD

The present disclosure generally relates to medical devices for the treatment of musculoskeletal disorders, and more particularly to a surgical system and a method for treating a spine.

BACKGROUND

Spinal disorders such as fracture, degenerative disc disease, disc herniation, osteoporosis, spondylolisthesis, stenosis, scoliosis and other curvature abnormalities, kyphosis, and tumor, may result from factors including trauma, disease and degenerative conditions caused by injury and aging. Spinal disorders typically result in symptoms including pain, nerve damage, and partial or complete loss of mobility.

Non-surgical treatments, such as medication, rehabilitation and exercise can be effective, however, may fail to relieve the symptoms associated with these disorders. Surgical treatment of these spinal disorders includes correction, fusion, fixation, osteotomy, discectomy, laminectomy and implantable prosthetics. Correction treatments used for positioning and alignment of vertebrae may employ implants, such as, for example, spinal constructs and interbody devices, for stabilization of a treated section of a spine. In some embodiments, the spinal constructs may be manipulated with surgical instruments for compression and distraction of vertebrae. This disclosure describes an improvement over these prior technologies.

SUMMARY

In one embodiment, a surgical instrument is provided. The surgical instrument includes a first arm engageable with a first spinal construct disposed with a first vertebral surface. A second arm is connected with the first arm via a pivot and is engageable with a second spinal construct disposed with a second vertebral surface. The first arm is movable to rotate the first spinal construct relative to the pivot and/or the second arm is movable to rotate the second spinal construct relative to the pivot such that the first vertebral surface is moved relative to the second vertebral surface. Systems and methods of use are disclosed.

BRIEF DESCRIPTION OF THE DRAWINGS

The present disclosure will become more readily apparent from the specific description accompanied by the following drawings, in which.

DETAILED DESCRIPTION

The exemplary embodiments of the system and related methods of use disclosed are discussed in terms of medical devices for the treatment of musculoskeletal disorders and more particularly, in terms of a surgical system and method for correction of a spine disorder. In some embodiments, the surgical system includes a surgical instrument configured to aide in restoration of lordosis and/or kyphosis. In some embodiments, the surgical system is employed with a method to treat a compression fracture of a vertebral body.

In some embodiments, the surgical system includes a surgical instrument that comprises a spinal rod instrument having a plurality of rods that rotate freely. In some embodiments, the spinal rod instrument has two rods that rotate freely. In some embodiments, rotation of the rods can be fixed by locking the rods together with a set screw. In some embodiments, the spinal rod instrument is provisionally implanted with a patient to aide in fracture correction. In some embodiments, the rods are employed with a method of selective correction of vertebrae such that the spinal rod instrument is removed and replaced with a permanently implantable rod.

In some embodiments, the surgical system is employed with a method for treatment of a spine that includes inserting bone screws with vertebrae. In some embodiments, the method includes the step of passing the spinal rod instrument through extenders adjacent the vertebrae. In some embodiments, the method includes the step of manipulating the vertebrae with attached bone screws via the spinal rod instrument to obtain correction of a spine disorder. In some embodiments, the step of manipulating includes a center of rotation of the manipulated vertebrae adjacent the vertebrae, such as, for example, adjacent a facet joint. In some embodiments, the method includes the step of provisionally implanting a second spinal rod instrument with the vertebrae on a contra-lateral side. Upon fixation of the second spinal rod instrument with the contra-lateral side of the vertebrae, the first spinal rod instrument is removed and replaced with a permanently implantable rod.

In some embodiments, the surgical system is employed with a method for implanting a fixed angle screw (FAS) above and below a vertebral fracture site and then employed for a correction treatment. In some embodiments, the spinal rod instrument includes a center of rotation positioned close to a vertebral body.

In some embodiments, the spinal rod instrument is configured as minimally invasive instrumentation for correction of a vertebral fracture. In some embodiments, the spinal rod instrument is employed to correct a vertebral fracture minimally invasively. In some embodiments, the spinal rod instrument includes a set screw configured to lock and unlock rotation of each rod. In some embodiments, the locking and un-locking of the set screw along with rotation of the rods allows for correction of the misplaced vertebrae due to an adjacent fractured vertebrae.

In some embodiments, the surgical system is employed with a method for treating a spine including the step of disposing a pedicle screw with vertebrae and inserting the spinal rod instrument using a rod inserter with the set screw facing up. In some embodiments, the surgical system is employed with a method for treating a spine including the step of engaging reducers and/or set screws to secure the spinal rod instrument in at least one screw head. In some embodiments, the surgical system is employed with a method for treating a spine including the step of locating the set screw disposed with the spinal rod instrument using fluoroscopy and unscrewing the set screw to allow for fracture correction. In some embodiments, the surgical system is employed with a method for treating a spine including the step of securing the set screw to fix the spinal rod instrument. In some embodiments, the surgical system is employed with a method for treating a spine including the step of securing a second spinal rod instrument into a screw head with the use of a reducer or set screw. In some embodiments, the surgical system is employed with a method for treating a spine including the step of loosening the set screw of the spinal rod instrument and allowing the spinal rod instrument to rotate down to the screw head.

In some embodiments, the surgical system is employed with a method for treating a spine including the step of manually or with a surgical instrument, such as, for example, a compressor and/or a distractor, rotating vertebrae until selected correction is obtained. In some embodiments, the surgical system is employed with a method for treating a spine including the step of locking the set screw of the spinal rod instrument in place. In some embodiments, the surgical system is employed with a method for treating a spine including the step of placing screws and a spinal rod instrument on a contra-lateral side of vertebrae. In some embodiments, the surgical system is employed with a method for treating a spine including the step of removing the spinal rod instrument from the patient and inserting an implant rod.

In some embodiments, the surgical system is employed with a method for treating a spine that can compress or distract and restore curvature of a spine. In some embodiments, the surgical instrument is used to restore vertebral body height and lordosis after a trauma, such as, for example, a fall or car accident. In some embodiments, the surgical instrument can attach to implant supports, such as, for example, screw extenders.

In some embodiments, the surgical system of the present disclosure may be employed to treat spinal disorders such as, for example, degenerative disc disease, disc herniation, osteoporosis, spondylolisthesis, stenosis, scoliosis and other curvature abnormalities, kyphosis, tumor and fractures. In some embodiments, the surgical system of the present disclosure may be employed with other osteal and bone related applications, including those associated with diagnostics and therapeutics. In some embodiments, the disclosed surgical system may be alternatively employed in a surgical treatment with a patient in a prone or supine position, and/or employ various surgical approaches to the spine, including anterior, posterior, posterior mid-line, direct lateral, postero-lateral, and/or antero-lateral approaches, and in other body regions. The surgical system of the present disclosure may also be alternatively employed with procedures for treating the lumbar, cervical, thoracic, sacral and pelvic regions of a spinal column. The surgical system of the present disclosure may also be used on animals, bone models and other non-living substrates, such as, for example, in training, testing and demonstration.

The surgical system of the present disclosure may be understood more readily by reference to the following detailed description of the embodiments taken in connection with the accompanying drawing figures, which form a part of this disclosure. It is to be understood that this application is not limited to the specific devices, methods, conditions or parameters described and/or shown herein, and that the terminology used herein is for the purpose of describing particular embodiments by way of example only and is not intended to be limiting. In some embodiments, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior".

As used in the specification and including the appended claims, "treating" or "treatment" of a disease or condition refers to performing a procedure that may include administering one or more drugs to a patient (human, normal or otherwise or other mammal), employing implantable devices, and/or employing instruments that treat the disease, such as, for example, micro discectomy instruments used to remove portions bulging or herniated discs and/or bone spurs, in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. Also, as used in the specification and including the appended claims, the term "tissue" includes soft tissue, ligaments, tendons, cartilage and/or bone unless specifically referred to otherwise.

Figure 1:
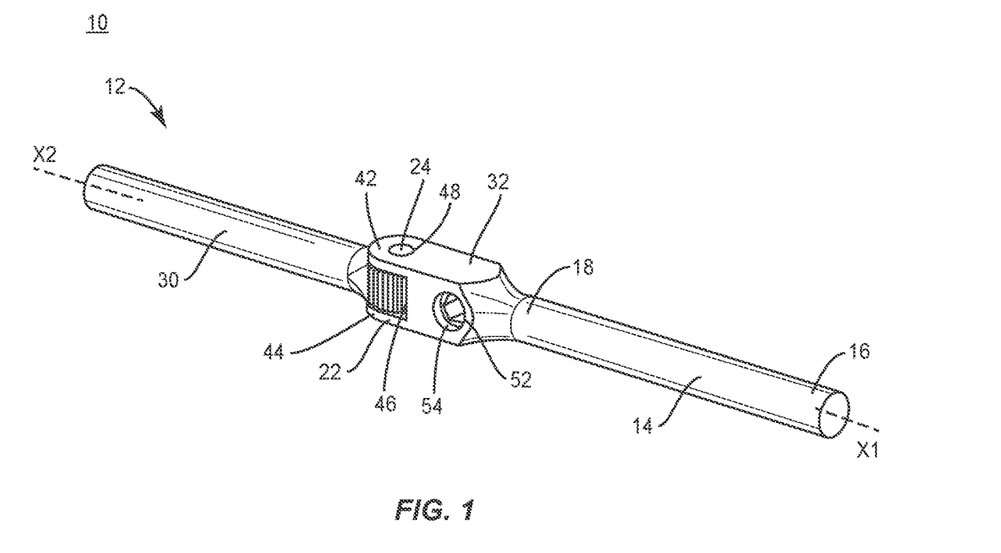
FIG. 1 is a perspective view of components of one embodiment of a surgical system in accordance with the principles of the present disclosure.
Figure 2:
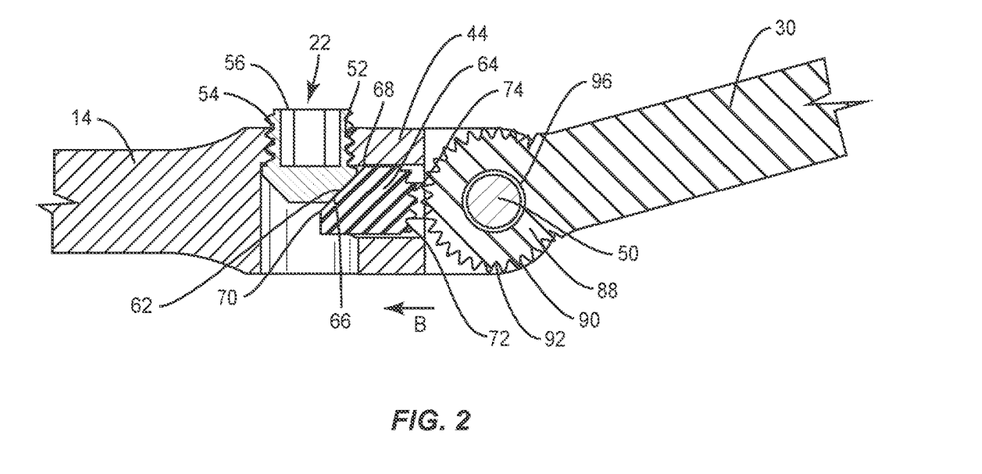
FIG. 2 is a break away cross section view of the components shown in FIG. 1.
Figure 3:
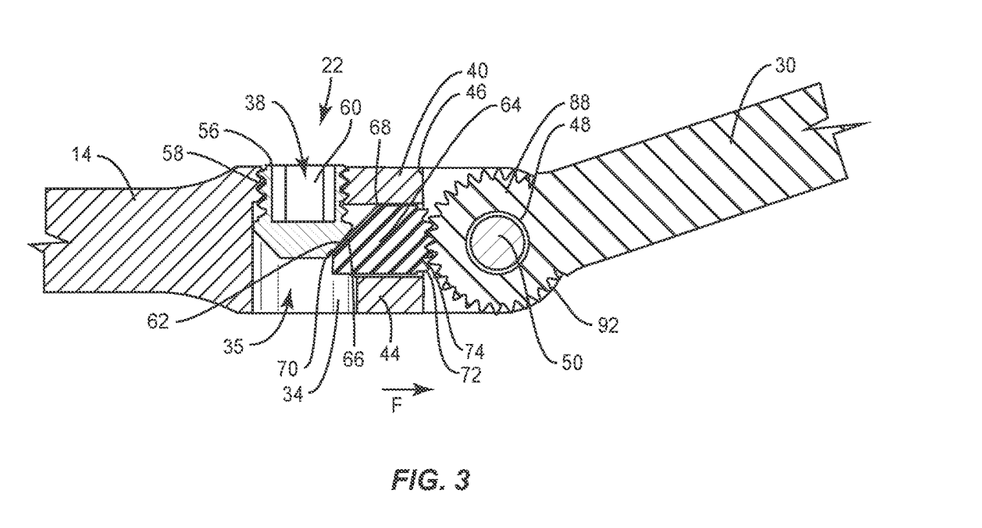
FIG. 3 is a break away cross section view of the components shown in FIG. 1.

The following discussion includes a description of a surgical system including implants, surgical instruments, related components and methods of employing the surgical system in accordance with the principles of the present disclosure. Alternate embodiments are also disclosed. Reference is made to the exemplary embodiments of the present disclosure, which are illustrated in the accompanying figures. Turning to FIGS. 1-3, there are illustrated components of a surgical system 10 including a surgical instrument 12.

The components of surgical system 10 can be fabricated from biologically acceptable materials suitable for medical applications, including metals, synthetic polymers, ceramics and bone material and/or their composites. For example, the components of surgical system 10, individually or collectively, can be fabricated from materials such as stainless steel alloys, aluminum, commercially pure titanium, titanium alloys, Grade 5 titanium, super-elastic titanium alloys, cobalt-chrome alloys, super elastic metallic alloys (e.g., Nitinol, super elasto-plastic metals, such as GUM METAL®), ceramics and composites thereof such as calcium phosphate (e.g., SKELITE™), thermoplastics such as polyaryletherketone (PAEK) including polyetheretherketone (PEEK), polyetherketoneketone (PEKK) and polyetherketone (PEK), carbon-PEEK composites, PEEK-BaSO$_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate, tri-calcium phosphate (TCP), hydroxyapatite (HA)-TCP, calcium sulfate, or other resorbable polymers such as polyaetide, polyglycolide, polytyrosine carbonate, polycaroplaetohe and their combinations.

Various components of surgical system 10 may have material composites, including the above materials, to achieve various desired characteristics such as strength, rigidity, elasticity, compliance, biomechanical performance, durability and radiolucency or imaging preference. The components of surgical system 10, individually or collectively, may also be fabricated from a heterogeneous material such as a combination of two or more of the above-described materials. The components of surgical system 10 may be monolithically formed, integrally connected or include fastening elements and/or instruments, as described herein.

The components of surgical system 10 are employed, for example, with an open or mini-open, minimal access and/or minimally invasive surgical procedure including percutaneous surgical techniques. For example, surgical instrument 12 can provide a temporary hold of one or more vertebral bodies during spinal procedures at a surgical site within a body of a patient, for example, a section of a spine to treat various spine pathologies, such as, for example, those described herein. In some embodiments, ends of surgical instrument 12 are placed into fasteners attached to vertebrae such that surgical instrument 12 comprises a temporary stabilizing device. In some embodiments, surgical instrument 12 is utilized to correct a vertebral fracture by manipulation of surgical instrument 12. In some embodiments, surgical instrument 12 includes a lock configured to maintain and/or measure an angle between the ends of surgical instrument 12 for employment with pedicle subtraction osteotomy (PSO) and/or vertebral column resection (VCR) procedures, as described herein. In some embodiments, surgical instrument 12 is employed to stabilize, measure and/or display an angle between vertebral bodies to determine configuration, dimension and/or orientation of a permanently implantable spinal rod with the vertebral bodies.

In some embodiments, surgical instrument 12 comprises a temporary and/or permanent implant configured for attachment to vertebrae during surgical treatment of a spinal disorder, as described herein. In some embodiments, one or a plurality of surgical instruments 12 may be attached with one or a plurality of vertebral levels in various orientations, such as, for example, parallel, perpendicular, angular, staggered and/or offset.

Figure 4:
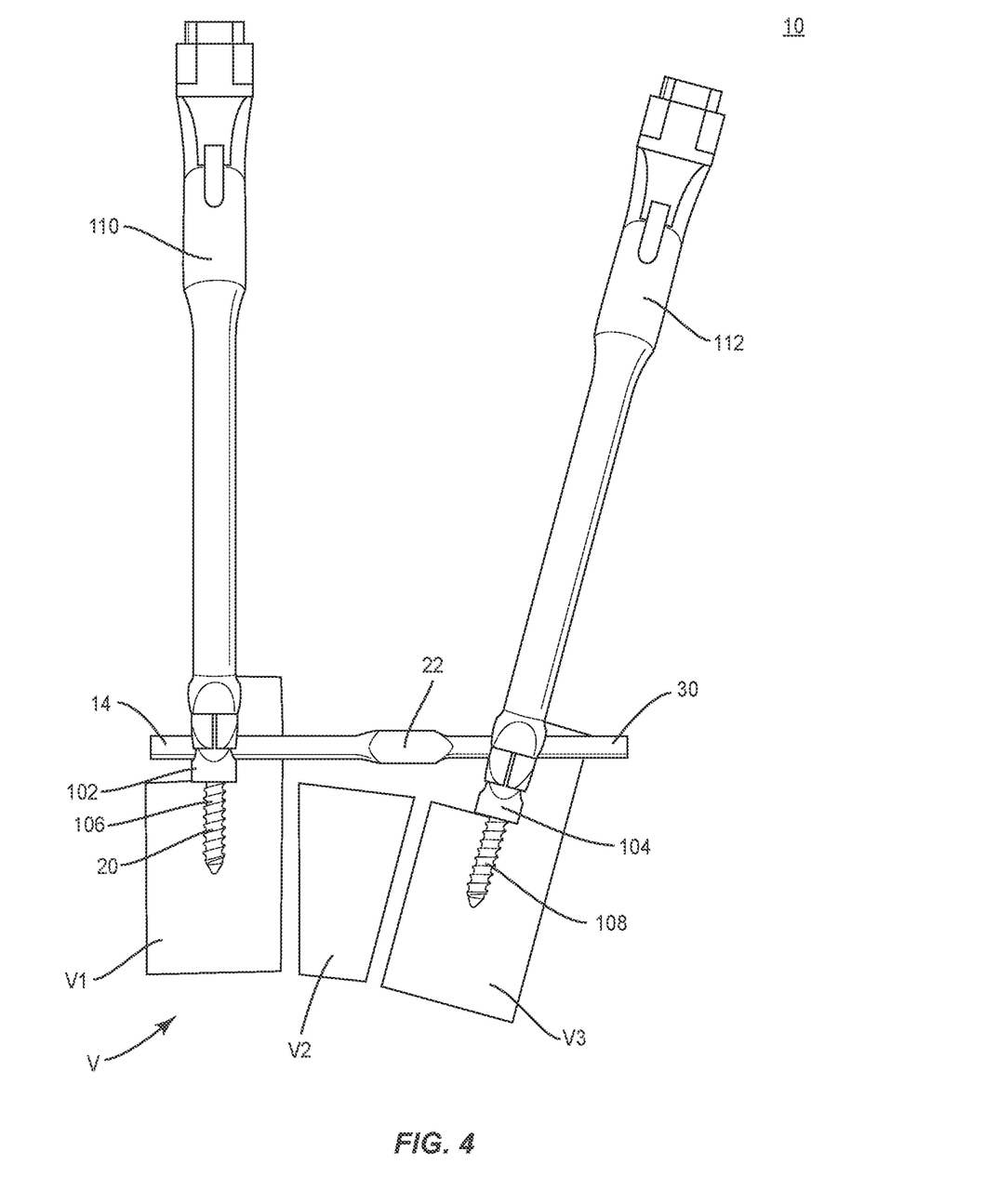
FIG. 4 is a side view of components of one embodiment of a surgical system in accordance with the principles of the present disclosure disposed with vertebrae.

Surgical instrument 12 includes an arm, such as, for example, a rod 14 that defines a longitudinal axis X1. Rod 14 extends between an end 16 and an end 18. End 16 is configured for engagement with a spinal construct, such as, for example, a bone screw, such as, for example, a FAS 20 (FIG. 4) disposed with a vertebral surface, as described herein. End 18 is connected with a body, such as, for example, a connector 22 having a pivot 24, as described herein.

Rod 14 is connected with connector 22 such that end 18 is monolithically formed with connector 22. In some embodiments, end 18 is attached, assembled, adhered, friction fit, interference fit, molded and/or threaded with connector 22. In some embodiments, rod 14 is attached with connector 22 in various orientations, such as, for example, series, parallel, perpendicular, angular, offset and/or staggered. In some embodiments, rod 14 is integrally connected with connector 22 or includes fastening elements and/or instruments for assembly with connector 22. Connector 22 is configured to connect rod 14 with an arm, such as, for example, a rod 30, as described herein.

In some embodiments, rod 14 may have various surface configurations, such as, for example, threaded for connection with surgical instruments, arcuate, undulating, dimpled, polished and/or textured. In some embodiments, the thickness defined by rod 14 may be tapered, uniformly increasing or decreasing, or have alternate diameter dimensions along its length. In some embodiments, all or only a portion of rod 14 may have various cross-section configurations, such as, for example, arcuate, cylindrical, oblong, rectangular, polygonal, undulating, irregular, uniform, non-uniform, consistent, variable, and/or U-shape.

Rod 14 is movable to rotate bone screw 20 relative to pivot 24 and/or rod 30. Rod 14 is moveable, such as, for example, pivotable or rotatable, to move a first vertebral surface relative to a second vertebral surface, as described herein, for treating a spinal disorder, as described herein.

Connector 22 includes an outer surface 32 and an inner surface 34. Inner surface 34 defines cavity 35. Cavity 35 is configured for disposal of a lock 38, as described herein. In some embodiments, outer surface 32 and inner surface 34 may have alternate surface configurations, such as, for example, rough, arcuate, undulating, mesh, porous, semi-porous, dimpled and/or textured.

Connector 22 includes a surface 40 that includes arms 42, 44. Arms 42, 44 extend in a bi-furcated configuration and a parallel orientation to define a cavity 46. Cavity 46 is in communication with cavity 35 to facilitate locking of rod 30 relative to pivot 24 and/or rod 14, as described herein.

Arms 42, 44 each include an opening 48 configured to receive a pin 50 aligned with and corresponding to the position and orientation of pivot 24. Pin 50 is disposed within openings 48 to facilitate relative rotation and/or pivoting of rods 14, 30. In some embodiments, arms 42, 44 may extend in alternate orientations from connector 22, such as, for example, converging, diverging, offset, staggered, angled and/or non-parallel. In some embodiments, connector 22 may include one or a plurality of arms extending therefrom.

Connector 22 includes a surface 52 that defines an opening 54. Opening 54 is configured for disposal and surface 52 is configured for engagement with an actuator, such as, for example, a set screw 56 of lock 38, as described herein. In some embodiments, surface 52 is threaded to facilitate engagement with a threaded surface 58 of set screw 56, as described herein. Set screw 56 includes a socket 60. In some embodiments, socket 60 includes a hexalobe geometry configured for disposal of a similarly shaped bit of a surgical tool, such as, for example, a driver, as described herein. In some embodiments, socket 60 has a cruciform, phillips, square, hexagonal, polygonal, star cross sectional configuration, configured for disposal of a correspondingly shaped portion of a driver.

Set screw 56 includes an angled surface 62 configured for slidable engagement with a wedge 64. Wedge 64 includes a surface 66. Surface 66 is angled and extends between an end 68 and an end 70. Wedge 64 includes a surface 72. Surface 72 includes a gear surface, such as, for example, splines 74 configured to engage splines 92 of rod 30, as described herein, to facilitate incremental and selective positioning of rod 30 for fixation of rod 30 relative to pivot 24 and/or rod 14 via relative movement of the respective gear surfaces, and locking of rod 30 relative to pivot 24 and/or rod 14 via mesh engagement of the respective gear surfaces. In some embodiments, splines 74 are laterally oriented and axially disposed along surface 72. In some embodiments, splines 92 are laterally oriented and circumferentially disposed about an end 84 of rod 30.

Set screw 56 is threaded with surface 52 and translatable relative to connector 22 such that surface 62 slidably engages surface 66 between ends 68, 70. Set screw 56 is disposable in an orientation with connector 22 and wedge 64 such that wedge 64 is spaced apart from rod 30 and splines 74 are disengaged from splines 92 such that lock 38 is disposed in an unlocked configuration, as shown in FIG. 2. In the unlocked configuration, rod 30 is selectively movable relative to pivot 24 and/or rod 14.

A driver is engageable with set screw 56, as described herein, adjacent socket 60 to move lock 38 between the unlocked configuration and a locked configuration. The driver engages socket 60 to translate set screw 56 such that surface 62 engages surface 66 to drive splines 74 into engagement with splines 92. Splines 74 mesh with splines 92 to dispose lock 38 in the locked configuration, as shown in FIG. 3, for incremental and selective fixation of rod 30 relative to pivot 24 and/or rod 14. In some embodiments, lock 38 includes a biasing element, such as, for example, a spring that biases wedge 64 to the unlocked configuration and/or the locked configuration. In some embodiments, wedge 64 can be manipulated via instrument and/or manual engagement.

Rod 30 defines a longitudinal axis X2. Rod 30 extends between an end 82 and end 84. End 82 is configured for engagement with a spinal construct, such as, for example, a bone screw, such as, for example, a FAS 36 (FIG. 4) disposed with a vertebral surface, as described herein.

End 84 is connected with connector 22 at pivot 24, as described herein. Rod 30 is connected with connector 22 such that end 84 is attached with connector 22 and rod 30 is rotatable and/or pivotable relative to pivot 24 and/or rod 14. In some embodiments, end 84 is assembled, adhered, friction fit, interference fit, molded, hinged and/or threaded with connector 22. In some embodiments, rod 30 is attached with connector 22 in various orientations, such as, for example, series, parallel, perpendicular, angular, offset and/or staggered. In some embodiments, rod 30 is integrally connected with connector 22 or includes fastening elements and/or instruments for assembly with connector 22.

End 84 includes a transverse cylindrical portion 88, as shown in FIGS. 2 and 3, which includes a surface 90. Surface 90 includes a gear surface, such as, for example, lateral splines 92. Splines 92 are configured for engagement with splines 74, as described herein. Engagement of splines 74 with splines 92 facilitates incremental and selective positioning of rod 30 and fixation of rod 30 relative to pivot 24 and/or rod 14. Portion 88 includes a surface 94 that defines an opening 96. Opening 96 is configured for disposal of pin 50, as described herein. Pin 50 is configured to facilitate attachment of rod 30 with connector 22, and rotation and/or pivoting of rod 30, as described herein.

In some embodiments, rod 30 and/or surface 90 may have various surface configurations, such as, for example, threaded for connection with surgical instruments, arcuate, undulating, dimpled, polished and/or textured. In some embodiments, the thickness defined by rod 30 may be tapered, uniformly increasing or decreasing, or have alternate diameter dimensions along its length.

Rod 30 is movable to rotate FAS 36 relative to pivot 24 and/or rod 14 to treat a spinal disorder, as described herein. Rod 30 is rotatable and/or pivotable relative to pivot 24 and/or rod 14, for example, to move a first vertebral surface relative to a second vertebral surface, as described herein. In some embodiments, rod 30 is rotatable and/or pivotable to a selected angle relative to pivot 24 and/or rod 14. In some embodiments, a center of rotation of pivot 24 is oriented adjacent vertebral levels, such as, for example, adjacent facet joints of vertebrae connected with rods 14, 30. In some embodiments, rod 30 is rotatable in a range of approximately 0-50 degrees relative to pivot 24 and/or rod 14. In some embodiments, rod 30 is rotatable relative to pivot 24 and/or rod 14 in a sagittal plane of a body.

Figure 9:
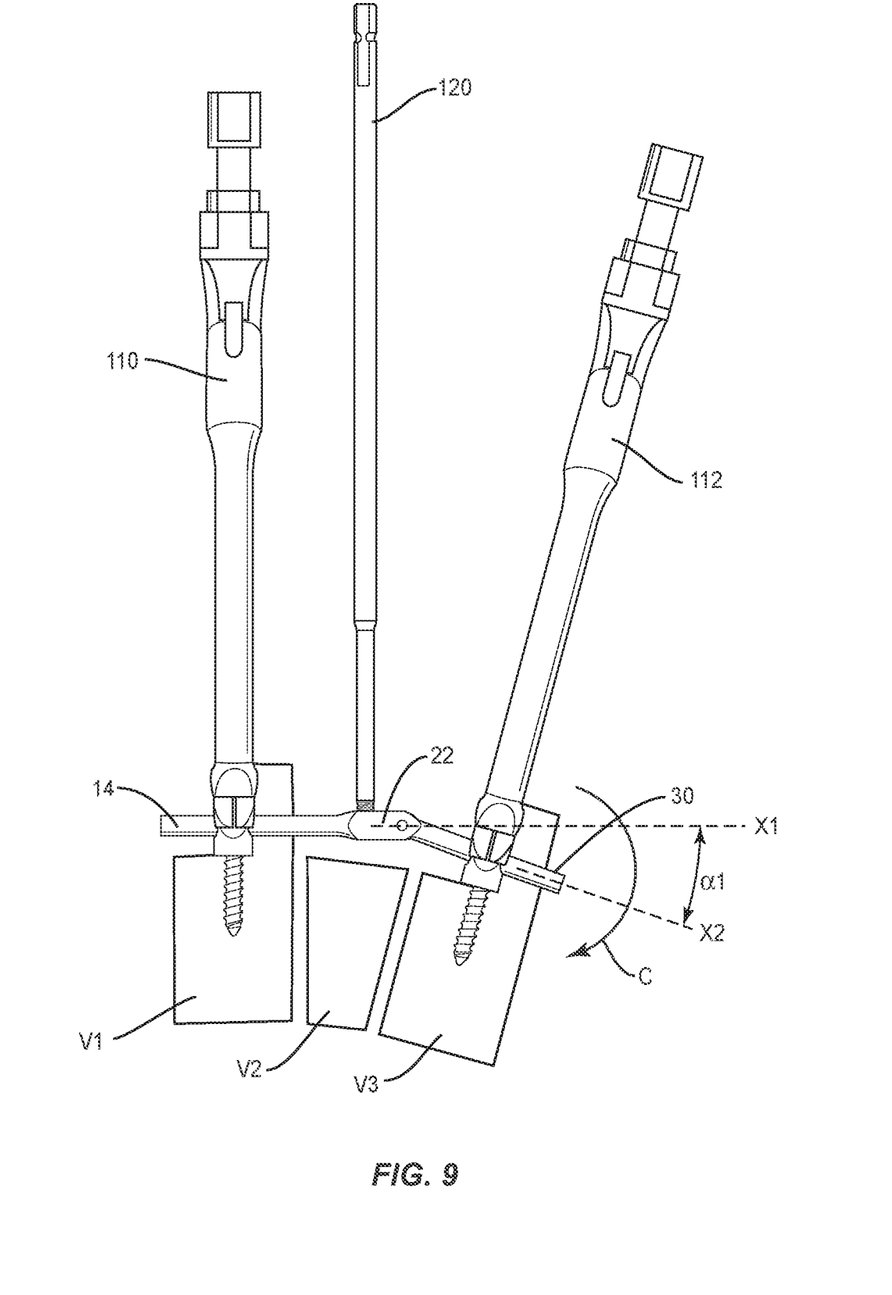
FIG. 9 is a side view of the components and vertebrae shown in FIG. 7.
Figure 12:
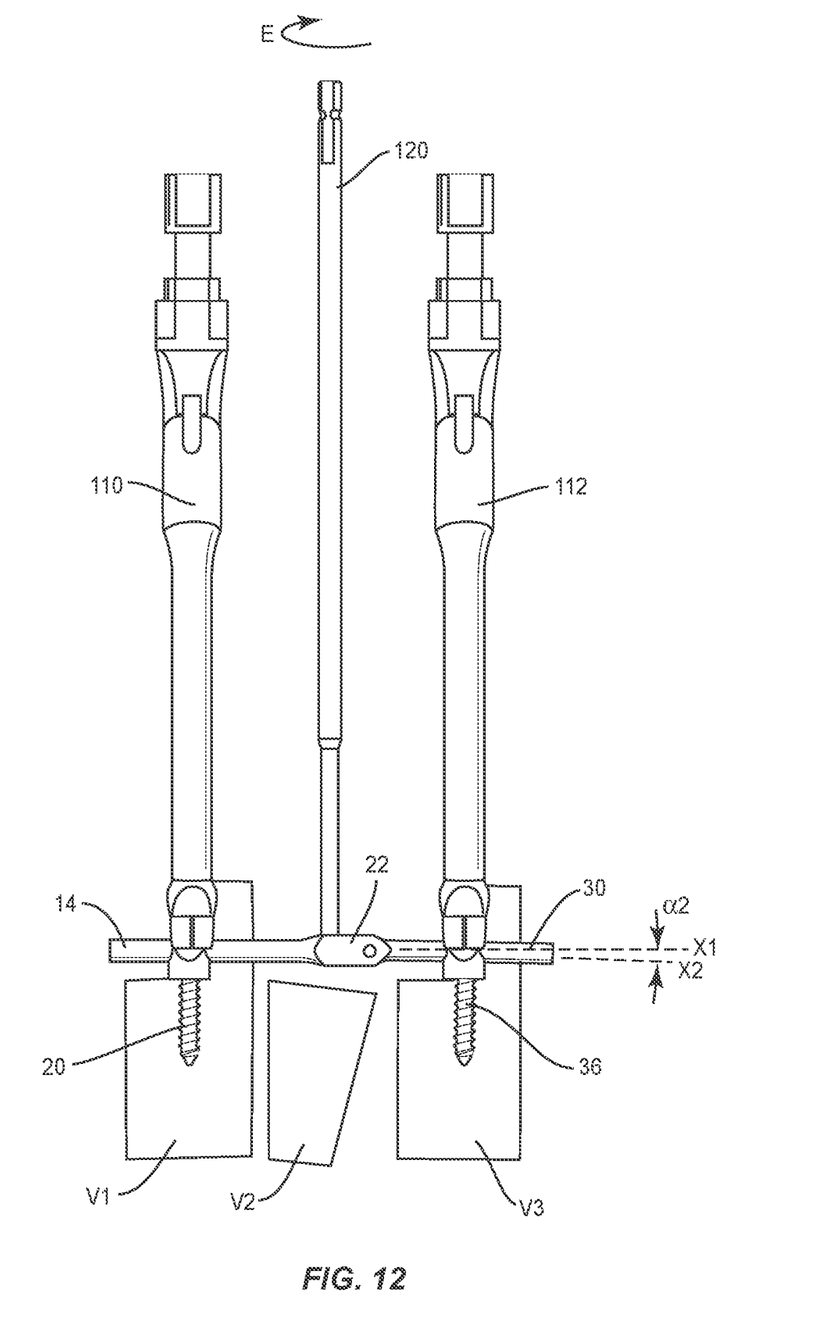
FIG. 12 is a side view of components of one embodiment of a surgical system in accordance with the principles of the present disclosure disposed with vertebrae.

For example, in some embodiments, FAS 20, 36 are connected with vertebrae and rods 14, 30, as described herein. Lock 38 is disposed in an unlocked configuration, as described herein. Rod 30 is disposed at an angle $\alpha 1$ relative to rod 14, as shown in FIG. 9. Rod 30 is selectively and/or incrementally rotated relative to pivot 24 and/or rod 14 to an angle $\alpha 2$, measured from their respective axes, X2, X1 Lock 38 is selectively locked, as described herein, to fix rods 14, 30 in a selected orientation at angle $\alpha 2$ and/or in a template configuration for a final and/or permanent implant rod, as shown in FIG. 12. In some embodiments, surgical instrument 12 includes a center of rotation, such as, for example, pivot 24 positioned close to the vertebrae connected with FAS 20, 36. In some embodiments, rods 14, 30 are adjustable to stabilize, measure and/or display angle $\alpha 2$ between rods 14, 30. In some embodiments, angle $\alpha 2$ is disposed such that axis X2 is coaxial with axis X1. In some embodiments, angle $\alpha 2$ is disposed such that axis X2 is transverse to axis X1.

In some embodiments, rod 14 is configured for disposal with FAS 20 attached to a first vertebra, and rod 30 is configured for disposal with FAS 36 attached to a second vertebra. In some embodiments, FAS 20 comprises a receiver 102 and FAS 36 comprises a receiver 104 configured to receive rods 14, 30. In some embodiments, FAS 20 comprises a shaft 106 and FAS 36 comprises a shaft 108 configured to engage tissue, such as, for example, vertebrae V. In some embodiments, FAS 20, 36 may be engaged with tissue in various orientations, such as, for example, series, parallel, offset, staggered and/or alternate vertebral levels. In some embodiments, surgical system 10 can include one or more bone screws that may comprise multi-axial screws, sagittal angulation screws, pedicle screws, mono-axial screws, uni-planar screws, facet screws, tissue penetrating screws, conventional screws, expanding screws, wedges, anchors, buttons, clips, snaps, friction fittings, compressive fittings, expanding rivets, staples, nails, adhesives, posts, fixation plates and/or posts.

In assembly, operation and use, surgical system 10 including surgical instrument 12, similar to the systems and methods described herein, is employed with a surgical procedure, such as, for example, a method for correction of deformities such as kyphosis or scoliosis, to treat a compression fracture of a vertebral body, fracture correction and/or a method for treating a patient with a PSO or a VCR. In some embodiments, one or all of the components of surgical system 10 can be delivered or utilized as a pre-assembled device or can be assembled in situ.

For example, surgical system 10, as shown in FIGS. 4-12, can be employed with a surgical correction treatment of a compression fracture of vertebrae V, which includes vertebral levels V1-V3, and adjacent areas within a body. In operation, to treat a condition of the spine, such as, for example, trauma of the spine, surgical instrument 12 is manipulated for engagement with extenders 110, 112 such that FAS 20, 36 are relatively movable for treatment of the vertebral fracture. In some embodiments, surgical instrument 12 is employed to treat vertebrae such that selected vertebra can be relatively translated for substantially axial compression or distraction to restore vertebral body height and rotated to achieve lordosis and restore curvature of the spine.

An incision is made in the body of a patient and a cutting instrument (not shown) creates a surgical pathway for implantation of components of surgical system 10. A preparation instrument (not shown) can be employed to prepare tissue surfaces of vertebrae V, as well as for aspiration and irrigation of a surgical region.

Pilot holes or the like are made in selected vertebra V1 and vertebra V3 of vertebrae V adjacent fractured vertebra V2 for receiving FAS 20, 36, with fractured vertebra V2 being disposed between vertebrae V1, V3. A driver (not shown) is disposed adjacent vertebrae V at a surgical site and is manipulated to drive, torque, insert or otherwise connect FAS 20, 36 adjacent vertebrae V1 and V3. Extenders 110, 112 are delivered to the surgical site adjacent vertebrae V and oriented for manipulation, alignment and capture of FAS 20, 36. Extender 110 is connected to FAS 20 and extender 112 is connected to FAS 36.

Figure 5:
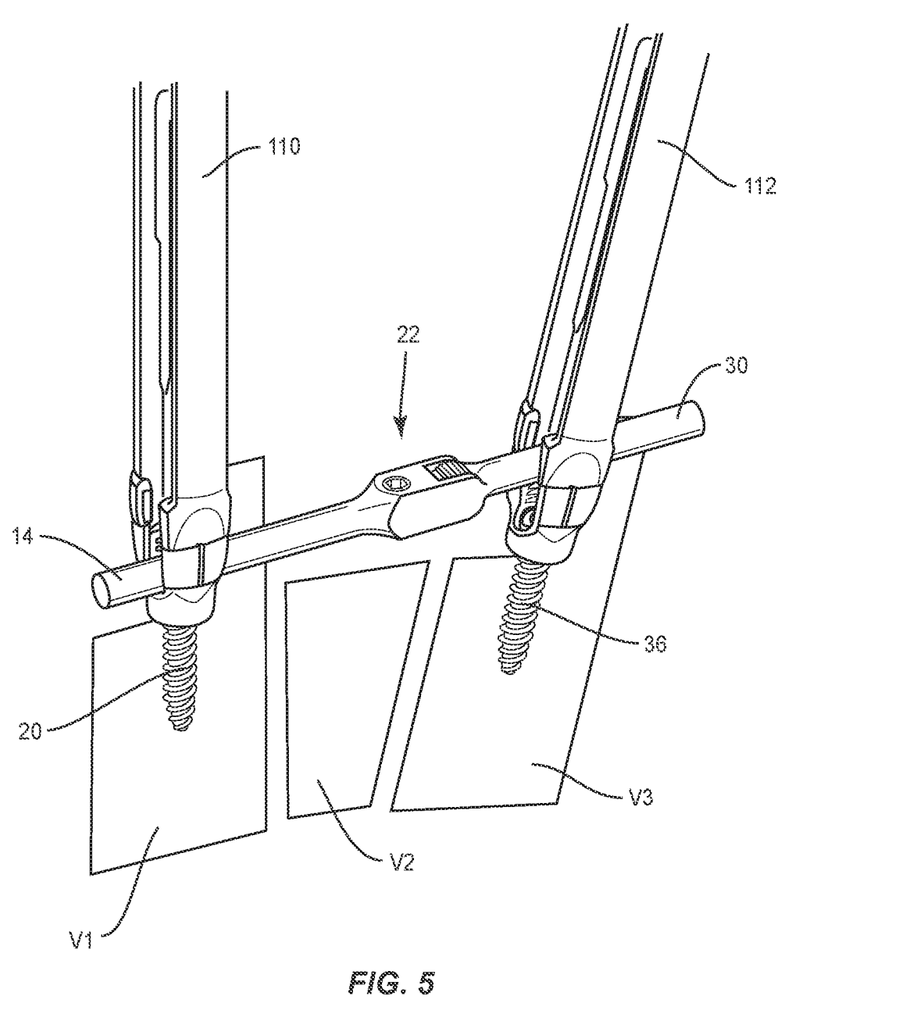
FIG. 5 is a perspective view of components of one embodiment of a surgical system in accordance with the principles of the present disclosure disposed with vertebrae.
Figure 6:
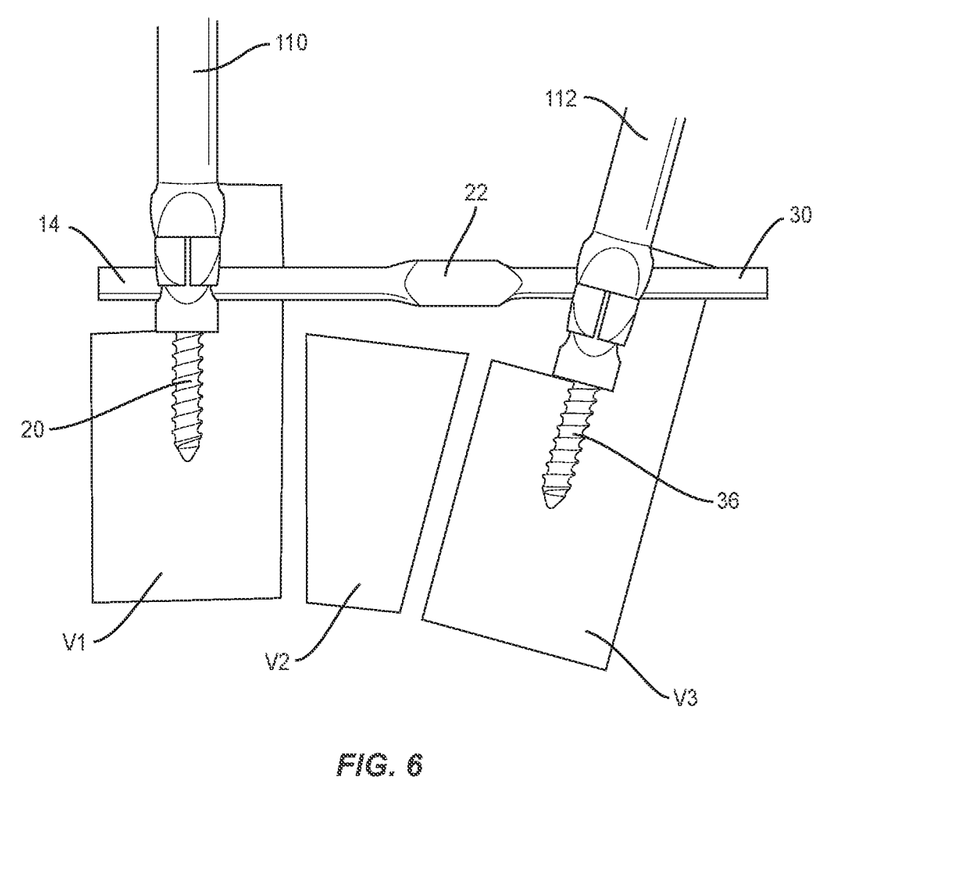
FIG. 6 is a perspective view of components of one embodiment of a surgical system in accordance with the principles of the present disclosure disposed with vertebrae.
Figure 7:
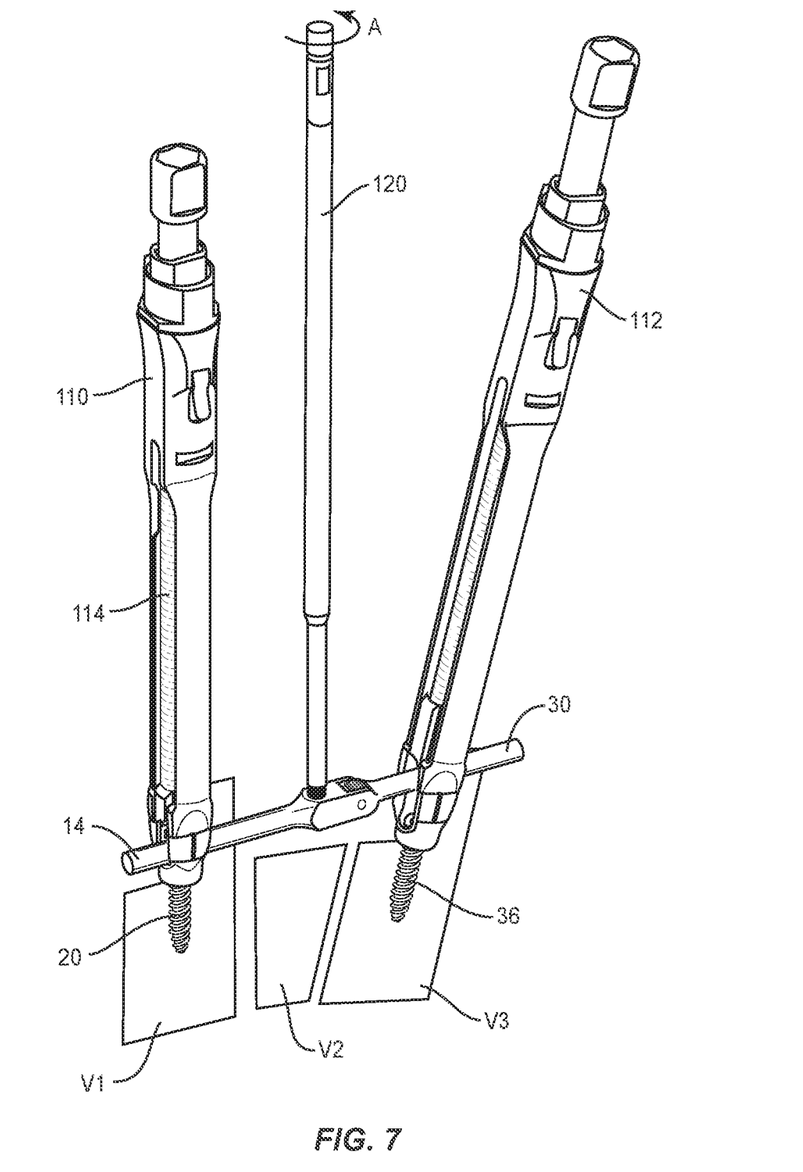
FIG. 7 is a perspective view of components of one embodiment of a surgical system in accordance with the principles of the present disclosure disposed with vertebrae.
Figure 8:
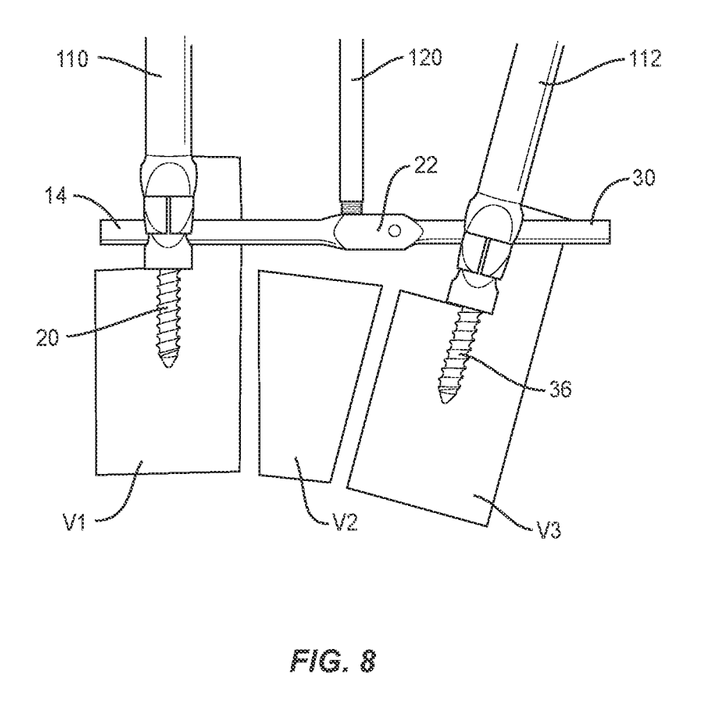
FIG. 8 is a break away view of the components and vertebrae shown in FIG. 7.

An inserter is connected with surgical instrument 12. Surgical instrument 12 is positioned such that opening 54 is oriented in a posterior orientation to facilitate manipulation of set screw 56, as shown in FIG. 5. Surgical instrument 12 is attached to a lateral side of vertebrae V such that rod 14 is inserted with receiver 102 of FAS 20 and rod 30 is inserted into receiver 104 of FAS 36, as shown in FIG. 6. A center of rotation of pivot 24 is oriented adjacent facet joints of vertebrae V1-3. Rod 14 is reduced with receiver 102 with a reducer 114, as shown in FIGS. 7 and 8. A set screw (not shown) is connected with FAS 20 or reducer 114 is employed to provisionally secure rod 14 with FAS 20.

Figure 10:
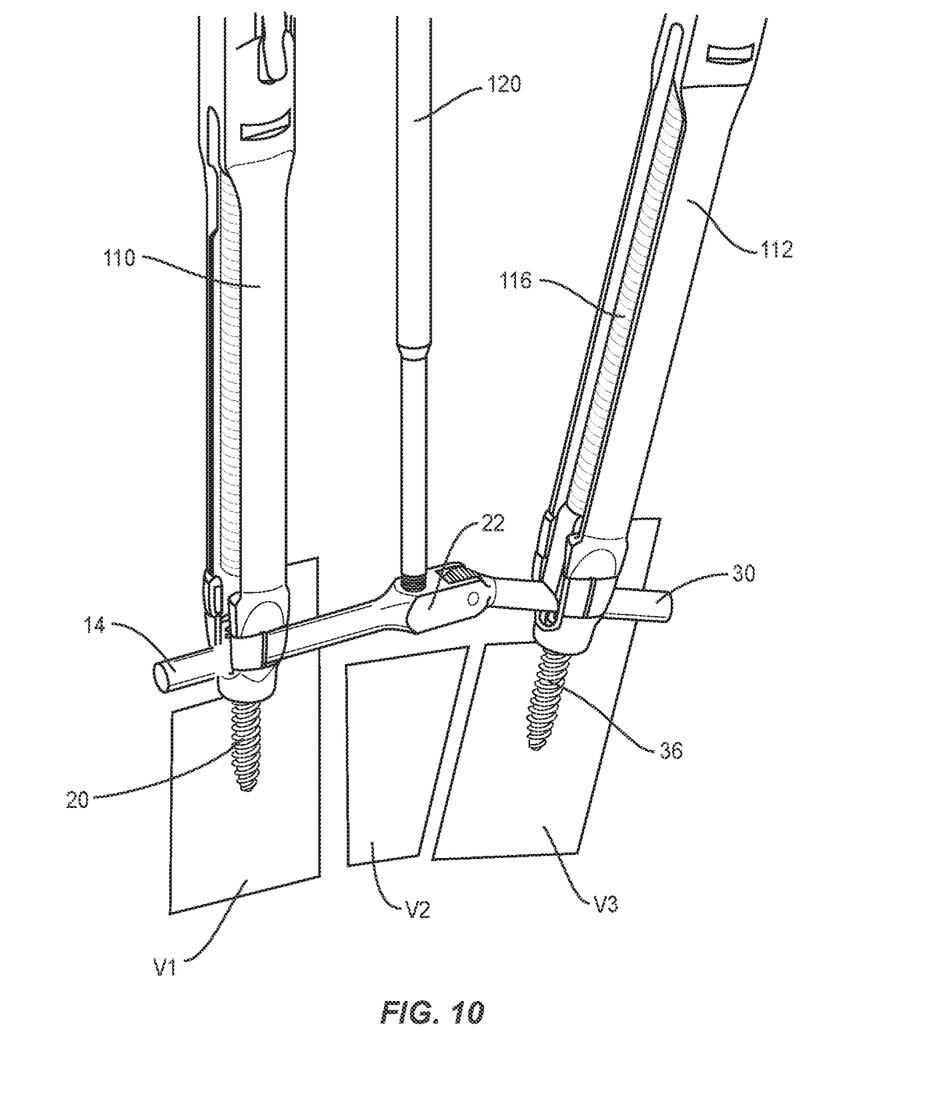
FIG. 10 is a perspective view of the components and vertebrae shown in FIG. 7.

Set screw 56 is rotated, in a direction shown by arrow A in FIG. 7, by a driver 120 to disengage set screw 56 from wedge 64 causing wedge 64 to translate, in a direction shown by arrow B in FIG. 2, and dispose lock 38 in an unlocked configuration. Rod 30 is freely rotatable relative to pivot 24 and/or rod 14. Rod 30 is selectively rotated, in a direction shown by arrow C in FIG. 9, into receiver 106 of FAS 36. Rod 30 is reduced with receiver 106 with a reducer 116, as shown in FIG. 10. Rod 30 is disposed at an angle α1 relative to rod 14, as shown in FIG. 9. A set screw (not shown) is connected with FAS 36 or reducer 116 is employed to provisionally secure rod 30 with FAS 36.

Figure 11:
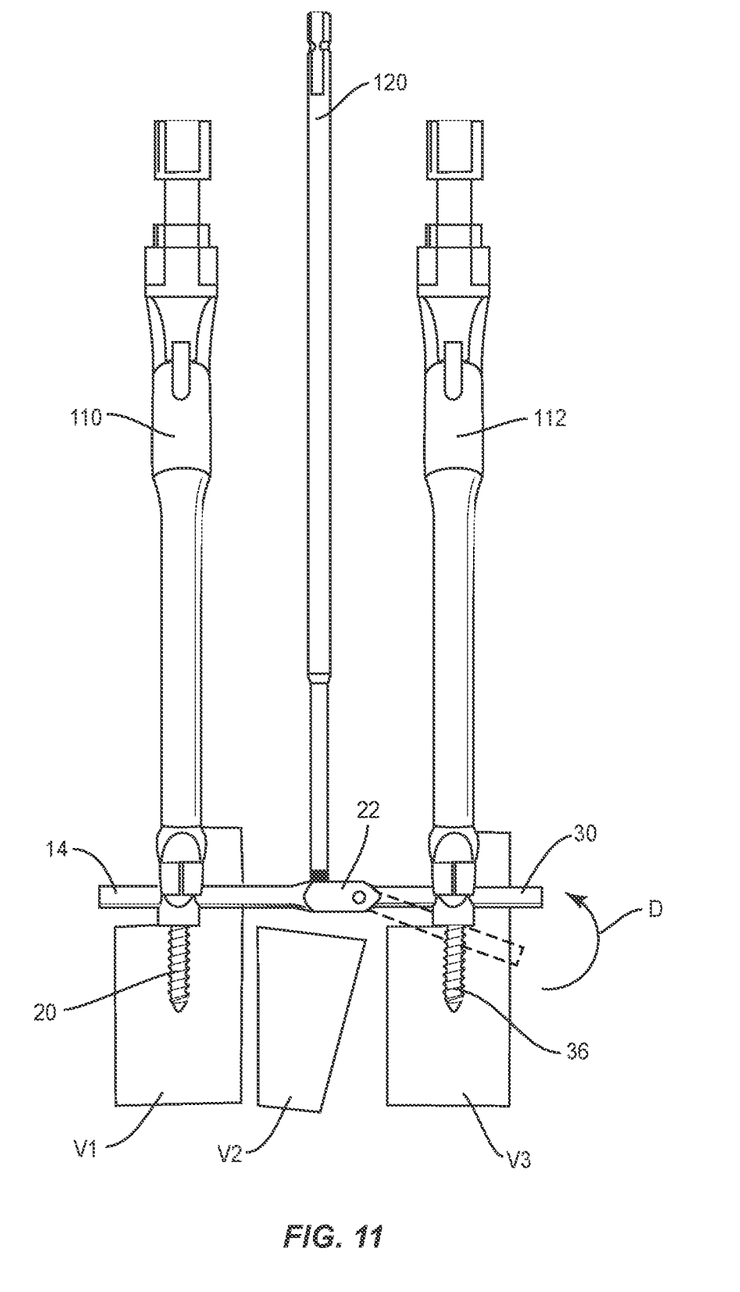
FIG. 11 is a side view of components of one embodiment of a surgical system in accordance with the principles of the present disclosure disposed with vertebrae.

A compressor or a distractor (not shown) is connected with extenders 110, 112 to manipulate rod 30 relative to pivot 24 and/or rod 14, in a direction shown by arrow D in FIG. 11, to rotate vertebra V3 relative to vertebrae V1 to correct fractured vertebrae V2. Rod 30 is selectively and incrementally rotated relative to pivot 24 and/or rod 14 to an angle α2 as shown in FIG. 12, measured from their respective axes, X2, X1, corresponding to a selected orientation of vertebrae V1-V3 for substantial axial compression or distraction to restore vertebral body height and rotated to achieve lordosis and restore curvature of the spine.

Set screw 56 is rotated by driver 120, in a direction shown by arrow E in FIG. 12, to dispose lock 38 in a locked configuration, as described herein, and fix orientation of rod 30 relative to pivot 24 and/or rod 14. Rotation of set screw 56 causes surface 62 to translate along surface 66 causing wedge 64 to translate, in a direction shown by arrow F in FIG. 3. Surface 62 engages surface 66 to drive splines 74 into engagement with splines 92. Splines 74 mesh with splines 92 to dispose lock 38 in the locked configuration for incremental and selective fixation of rod 30 relative to pivot 24 and/or rod 14 at angle α2, as shown in FIG. 12. Surgical instrument 12 is temporarily fixed with vertebrae V, as described above, to temporarily stabilize and fix vertebrae V in the selected orientation to correct vertebrae V. In some embodiments, rods 14, 30 are adjusted to stabilize, measure and/or display angle α2 between rods 14, 30 and/or selected vertebra of vertebrae V.

Surgical instrument 12 remains attached with FAS 20, 36 along the lateral side of vertebrae V to maintain temporary stabilization of vertebrae V. In some embodiments, bone screws and a permanent rod are engaged with a contralateral side of vertebrae V. In some embodiments, surgical instrument 12 is removed from the lateral side of vertebrae V and a permanent rod is engaged with bone screws 20, 36.

In some embodiments, surgical system 10 may include and/or be employed with various bone fasteners, including those described herein and for example, anchors, expanding screws, wedges, clips, friction fittings, compressive fittings, expanding rivets, staples, nails, fixation plates and/or posts. In various embodiments, the use of microsurgical and image guided technologies may be employed to access, view and repair spinal deterioration or damage, with the aid of surgical system 10. Upon completion of the procedure, the non-implanted components, surgical instruments and assemblies are removed and the incision is closed.

In some embodiments, surgical system 10 may comprise various surgical instruments, such as, for example, drivers, extenders, reducers, spreaders, distracters, blades, clamps, forceps, elevators and drills, which may be alternately sized and dimensioned, and arranged as a kit. In some embodiments, surgical system 10 may comprise the use of microsurgical and image guided technologies, such as, for example, surgical navigation components employing emitters and sensors, which may be employed to track introduction and/or delivery of the components of surgical system 10 including the surgical instruments to a surgical site.

In one embodiment, surgical system 10 includes an agent, which may be disposed, packed, coated or layered within, on or about the components and/or surfaces of surgical system 10. In some embodiments, the agent may include bone growth promoting material, such as, for example, bone graft to enhance fixation of the components and/or surfaces of surgical system 10 with vertebrae. In some embodiments, the agent may include one or a plurality of therapeutic agents and/or pharmacological agents for release, including sustained release, to treat, for example, pain, inflammation and degeneration.

In some embodiments, the components of surgical system 10 may be employed to treat progressive idiopathic scoliosis with or without sagittal deformity in either infantile or juvenile patients, including but not limited to prepubescent children, adolescents from 10-12 years old with continued growth potential, and/or older children whose growth spurt is late or who otherwise retain growth potential. In some embodiments, the components of surgical system 10 and method of use may be used to prevent or minimize curve progression in individuals of various ages.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. A surgical instrument comprising:
a first arm engageable with a first spinal construct configured to be disposed with a first vertebral surface;
a second arm connected with the first arm via a pivot and being engageable with a second spinal construct configured to be disposed with a second vertebral surface; and
a lock, the first arm including a connector that is monolithically formed with a rod of the first arm, the lock including a wedge that is disposed within the connector,
the first arm being movable to rotate the first spinal construct relative to the pivot and/or the second arm being movable to rotate the second spinal construct relative to the pivot such that the surgical instrument is movable between a first orientation in which the second arm is coaxial with the first arm and a second orientation in which the second arm extends transverse to the first arm.

2. A surgical instrument as recited in claim 1, further comprising a body monolithically formed with the first arm.

3. A surgical instrument as recited in claim 2, wherein the second arm is attachable to the body.

4. A surgical instrument as recited in claim 1, wherein the connector comprises spaced apart first and second flanges, an end of the second arm being positioned between the flanges, the surgical instrument comprising a pin that extends through the flanges and an the end of the second arm, the pin defining the pivot.

5. A surgical instrument as recited in claim 1, wherein the second arm includes a second rod.

6. A surgical instrument as recited in claim 1, wherein the wedge includes a first end having a ramped surface and an opposite second end having a splined surface, the second arm including splines configured for engagement with the splined surface for selective locking of the second arm.

7. A surgical instrument as recited in claim 6, further comprising an actuator removably disposed with the connector, the actuator comprising an angled surface that is configured to engage the ramped surface to move the wedge relative to the second arms such that the splined surface engages the splines of the second arm.

8. A surgical instrument as recited in claim 7, wherein the first arm is free of splines.

9. A surgical instrument as recited in claim 6, wherein the connector is fixed to a rod of the first arm and comprises spaced apart first and second flanges, an end of the second arm being positioned between the flanges, the surgical instrument comprising a pin that extends through the flanges and an the end of the second arm, the pin defining the pivot.

10. A surgical instrument as recited in claim 9, wherein the pin extends through opposite inner and outer surfaces of the flanges, the outer surfaces facing away from one another.

11. A surgical instrument as recited in claim 1, wherein the first arm defines a longitudinal axis and the second arm is rotatable to one or a plurality of axes relative to the longitudinal axis.

12. A surgical instrument as recited in claim 1, further comprising a driving instrument configured to facilitate pivoting of the second arm.

13. A surgical instrument comprising:
a first rod engageable with a first bone screw configured to be disposed with a first vertebral surface;
a second rod connected with the first rod via a pivot and being engageable with a second bone screw configured to be disposed with a second vertebral surface;
a body; and
a lock disposed with the body, the lock including a wedge and an actuator, the wedge being movable relative to the rods, the wedge including splines configured to engage splines disposed on the second rod for selective locking of the second rod,
the first rod being movable to rotate the first bone screw relative to the pivot and/or the second rod being movable to rotate the second bone screw relative to the pivot such that the surgical instrument is movable between a first orientation in which the second rod is coaxial with the first rod and a second orientation in which the second rod extends transverse to the first rod.

14. A surgical instrument as recited in claim 13, wherein the actuator is configured to translate relative to the wedge to urge the wedge into engagement with the second rod.

15. A surgical system comprising:
a first bone screw configured to be disposed with a first vertebral surface;
a second bone screw configured to be disposed with a second vertebral surface;
a first arm engageable with the first bone screw;
a second arm connected with the first arm via a pivot and being engageable with the second bone screw; and
a lock, the first arm including a connector that is monolithically formed with a rod of the first arm, the lock including a wedge that is disposed within the connector,
the first arm being movable to rotate the first bone screw relative to the pivot and/or the second arm being movable to rotate the second bone screw relative to the pivot such that the surgical instrument is movable between a first orientation in which the second arm is coaxial with the first arm and a second orientation in which the second arm extends transverse to the first arm.

16. A surgical system as recited in claim 15, further comprising a first extender configured for attachment with the first bone screw and a second extender configured for attachment with the second bone screw.

17. A surgical system as recited in claim 15, further comprising a driving instrument to actuate locking and unlocking of the second arm.

\* \* \* \* \*

UNITED STATES PATENT AND TRADEMARK OFFICE
CERTIFICATE OF CORRECTION

Page 1 of 1

PATENT NO. : 10,004,538 B2
APPLICATION NO. : 15/140219
DATED : June 26, 2018
INVENTOR(S) : McNab et al.

It is certified that error appears in the above-identified patent and that said Letters Patent is hereby corrected as shown below:

On the Title Page

In Column 1, under "Notice", Line 3, delete "0 days. days." and insert -- 0 days. --, therefor.

In the Specification

In Column 8, Line 47, delete "X1 Lock" and insert -- X1. Lock --, therefor.

In Column 10, Line 59, delete "distracters," and insert -- distractors, --, therefor.

In the Claims

In Column 11, Line 56, in Claim 4, delete "an the end" and insert -- at the end --, therefor.

In Column 12, Line 11, in Claim 9, delete "an the end" and insert -- at the end --, therefor.

Signed and Sealed this
Twenty-ninth Day of January, 2019

Andrei Iancu
*Director of the United States Patent and Trademark Office*